United States Patent
Walker et al.

(12)

(10) Patent No.: US 6,355,777 B1
(45) Date of Patent: Mar. 12, 2002

(54) P43 ANTIGEN FOR THE IMMUNODIAGNOSIS OF CANINE EHRLICHIOSIS AND USES THEREOF

(75) Inventors: David H. Walker; Jere W. McBride, both of Galveston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/561,322

(22) Filed: Apr. 28, 2000

(51) Int. Cl.$^7$ ........................... C07K 1/00; A61K 39/00; A61K 29/002; C07H 21/02; C07H 21/04

(52) U.S. Cl. ................. 530/350; 424/184.1; 424/185.1; 424/190.1; 424/191.1; 424/192.1; 424/206.1; 424/234.1; 424/265.1; 435/41; 435/70.1; 435/71.1; 435/91.1; 530/300; 536/23.1; 536/23.7

(58) Field of Search ........................... 424/184.1, 185.1, 424/190.1, 191.1, 192.1, 200.1, 234.1, 265.1; 435/41, 70.1, 71.1, 91.1; 530/300, 350; 536/23.1, 23.7

(56) References Cited

U.S. PATENT DOCUMENTS 6,043,085 A * 3/2000 Yu et al. ...................... 435/325

\* cited by examiner

*Primary Examiner*—Rodney P. Swartz
(74) *Attorney, Agent, or Firm*—Benjamin Aaron Adler

(57) ABSTRACT

Canine monocytic ehrlichiosis, caused by *Ehrilichia canis* is a potentially fatal disease of dogs that requires rapid and accurate diagnosis in order to initiate appropriate therapy leading to a favorable prognosis. In the invention described herein, a new immunoreactive *E. canis* surface protein gene of 1170-bp was cloned, which encodes a protein with a predicted molecular mass of 42.6 kilodaltons (P43). The P43 gene was not found in *E. chaffeensis* DNA by Southern blot, and antisera against recombinant P43 (rP43) did not react with *E. chaffeensis* by IFA. The P43 was located on the surface of *E. canis* by immunoelectron microscopy. Forty-two dogs exhibiting signs and/or hematologic abnormalities associated with canine ehrlichiosis were tested by IFA and by Western immunoblot. Among the 22 samples that were IFA positive for *E. canis,* 100% reacted with the rP43, 96% with the rP28, and 96% with the rP140. The specificity of the recombinant proteins compared to IFA was 96% for rP28, 88% for P43 and 63% for P140. Results of this study demonstrate that the rP43 and rP28 are sensitive and reliable serodiagnostic antigens for the diagnosis of *Ehrlichia canis* infections.

6 Claims, 7 Drawing Sheets

A1             GCTTCCCCCAAGC TTAA5'    EcoRI    (SEQ ID NO: 3)
B1  Hpa II/HinP I   5'CG CGAAGGGGTTCG           (SEQ ID NO: 4)

A2             GCTTCCCCCAAGC CTTAA5'   EcoRI    (SEQ ID NO: 5)
B2  Hpa II/HinP I   5'CG CGAAGGGGTTCG G         (SEQ ID NO: 6)

A3             GCTTCCCCCAAGC CCTTAA5'  EcoRI    (SEQ ID NO: 7)
B3  Hpa II/HinP I   5'CG CGAAGGGGTTCG GG        (SEQ ID NO: 8)

Fig. 1

```
ATGTCAGATCCAAAACAAGGTGATCCAGAGAACAAAATCAAACTAACCCTAGTGGTGATATTCAGGATCAAAGTCAG    75
 M  S  D  P  K  Q  G  D  P  E  Q  N  Q  T  N  P  S  G  D  I  Q  D  Q  S  Q
CAAGATCAACAGGAACAAGATCAGCAGGAGCAGTTGGTGCTGTTGGTAATAGTCCTATTGAAAGAGAG              150
 Q  D  Q  Q  E  Q  D  Q  Q  E  Q  G  A  V  G  G  N  S  P  I  E  R  E
AGAGTAGCTGCTCCTGAGAGTGAAGATTTATATCGTGATTATACTGTAAAGAACTGCTGCTCCAATT               225
 R  V  A  A  P  E  S  E  D  L  Y  T  V  I  I  P  K  G  K  R  T  A  P  I
TTGGAAAGAAGTCTCCTACTCCTGAACCGAAAGTAGAAGATGATGAAGATTTACCTCCTACATTACCGCCAAGA        300
 L  E  R  K  S  P  T  P  E  P  K  V  E  D  D  E  D  L  P  P  T  L  P  P  R
ACATTTCAGGAGAAGGATATGATGACGTTGGAGTTGTAGTGTCCATGCCTACTGTTAGTCGTGGCATATACCAACTCCC   375
 T  F  S  G  E  G  Y  D  D  V  G  V  V  S  M  P  T  V  S  R  G  I  Y  Q  P  P
ATAGTTCAAGATAGTAATCTATATTCAAGTTCAATATTGGTGCCTCAAGAAGCACAATATGATCAGCAGCTCGG        450
 I  V  Q  D  S  N  L  Y  S  S  I  G  G  V  P  Q  E  A  Q  Y  D  A  A  A  R
GCTGGTGGGCCAAGAAGATTTTTGTATGGGCCATATACATTCAGTAATGGTCAGAAATTATGGACTTTGAATTT        525
 A  G  G  P  R  K  F  L  Y  G  P  Y  T  F  S  N  G  Q  E  I  M  D  F  E  F
GATACTCCTTGGCCAGATGTTAGGAATGCAGTTTTAGGTAATAAAGAAGAGTAGTAACTACTTCT                 600
 D  T  P  W  P  D  V  R  N  A  V  L  G  N  K  E  I  K  E  E  W  L  T  T  S
GGGCCAGTACGTGATATTGCTGATAGGATAGTTGCTTCTAAAGGTATTGTCTGAGGATCAAGTAGAAGAAATC         675
 G  P  V  R  D  I  A  D  R  I  V  A  S  K  G  D  L  S  E  D  Q  V  E  E  I
CTTGATATTATATTATGAATGAATCAGAAATCAGCTGAAGGTATTTCTAATCCATTACATGCTGATGTTGATAAT       750
 L  D  I  I  F  M  N  E  S  E  I  A  E  G  I  S  N  P  L  H  A  D  V  D  N
AATCCTGTTAAAGGTGCTAAGAATGTGATGACATTGATGACATTGAGTTTATGCATGTTGATCATGTTGATGTTGATAGTGAG  825
 N  P  V  K  G  A  K  N  V  M  T  L  M  H  L  V  Y  A  C  D  V  D  P  R  I
GTAAAGCTTTAGGAGAGTGGAAAATGATGAAGGTGATTAGGAGCTAAGTGTTAAAGCTTTGTATGGAGAAACAAAG      900
 V  K  A  L  G  E  V  E  N  D  E  G  D  L  G  A  N  A  Y  N  V  L  D  S  E
GGTAATCTTCCTTTACATCATGCTGCAAAGAATTGTGAAGGGATAATGTACAGGGGATAAGTTAAGCTTTGTATGGAAAACAAAG  975
 G  N  L  P  L  H  H  A  A  K  N  C  T  G  D  K  L  K  L  C  M  E  K  T  K
ACTGATTTTATTGATACTGCAAATTTGCGAATCAATCCCTTTACATATTATTACACAGAAGCCAGATTGTTCT        1050
 T  D  F  I  D  T  A  N  F  A  N  Q  S  P  L  H  I  T  Q  K  P  D  C  S
GTATTAGATATTGAAGAGTTTACAAGCCGTAATTTAGATTTTGGACTTGTAGATGGAGATGGTAAAAATCCTTTA      1125
 V  L  D  I  E  E  F  T  S  R  N  L  D  F  G  L  V  D  G  D  G  K  N  P  L
CATCGTGTTGAACATTTGCCACCTGTTAACTTAAAGGGGCGGTAA      1173  (SEQ ID No. 1)
 H  H  A  V  E  H  L  P  P  V  N  L  K  G  R             (SEQ ID No. 2)
```

P43 ANTIGEN FOR THE IMMUNODIAGNOSIS OF CANINE EHRLICHIOSIS AND USES THEREOF

FEDERAL FUNDING LEGEND

This invention was produced in part using funds from the Federal government under Grant No. AI31431 from the National Institute of Allergy and Infectious Diseases. Accordingly, the Federal government has certain rights in this invention.

BACKGROUND OF THE INVENTION

1. Field of the Invention

The present invention relates generally to the fields of molecular immunology and immunodiagnosis. More specifically, the present invention relates to a surface protein from *Ehrlichia canis*, P43, useful as an antigen in the immunodiagnosis of Canine Ehrlichiosis.

2. Description of the Related Art

Canine monocytic ehrlichiosis is a potentially fatal tick-borne disease of dogs with worldwide distribution caused primarily by the rickettsial agent, *Ehrlichia canis* (8). *E. canis* is an obligately intracellular bacterium that exhibits tropism for monocytes and macrophages (13), and establishes persistent infections in the vertebrate host (7). The disease is characterized by three stages: the acute stage which lasts 2 to 4 weeks, the subclinical stage, in which dogs can remain persistently infected for years, but do not exhibit clinical signs, followed by the chronic phase, where in many dogs the disease becomes progressively worse due to bone marrow hypoplasia and the prognosis less favorable (19). Treating the disease in the acute phase is important for the best prognosis, but clinical presentation of canine ehrlichiosis is non-specific making diagnosis difficult. Hematologic abnormalities such as leukopenia and thrombocytopenia often provide useful evidence of canine ehrlichiosis and are important factors in the initial diagnosis (19).

Diagnosis of canine ehrlichiosis by serologic methods such as the indirect fluorescent-antibody (IFA) test has become the standard method due to its simplicity, reliability and cost effectiveness (19). However, shortcomings of the indirect fluorescent-antibody test include the inability to make a species-specific diagnosis due to antigenic cross reactivity with other closely related Ehrlichia species that infect dogs (*E. chaffeensis, E. ewingii, E. equi*, and *E. platys*), subjective interpretations, which may result in false-negative results, or false-positives caused by cross-reactive antigens. Other diagnostic methods such as polymerase chain reaction (PCR) have been developed for specific detection of *E. canis*, and were reported to be more sensitive than cell culture isolation, but this method requires specialized training and expensive equipment (9). Isolation of the organism is time consuming, and only a few laboratories have been consistently successful with this method. Furthermore, additional tests characterizing the isolate are required for defining a specific etiology using this method.

Serologically cross-reactive antigens shared between *E. canis* and *E. chaffeensis* have been reported. Some of the major serologically cross-reactive proteins exhibit molecular masses of 28–30-kDa (1, 16), and it is now known that these proteins are encoded by homologous multigene families (14, 15). There are 21 and 5 homologous, but nonidentical, p28 genes that have been identified and sequenced in *E. chaffeensis* and *E. canis*, respectively (11, 28). Similar intraspecies and interspecies strain homology was observed between the P28 proteins of *E. canis* and *E. chaffeensis*, explaining the serologic cross reactivity of these proteins (10). A recent report demonstrated that the rP28 protein from *E. chaffeensis* was an insensitive tool in diagnosing cases of human monocytotrophic ehrlichiosis (HME) (25). The underlying reason appears to be the variability of the P28 protein among different strains of *E. chaffeensis* (27). Conversely, the P28 genes identified in *E. canis* are conserved among geographically dispersed strains (10, 11), and the *E. canis* rP28 has proven to be useful for diagnosis of canine ehrlichiosis (10, 14). Other homologous immunoreactive proteins including the glycoproteins P140 and P120 in *E. canis* and *E. chaffeensis*, respectively, have been cloned (24, 26). Reactivity of the rP120 of *E. chaffeensis* has correlated well with the IFA for serodiagnosis of human monocytotropic ehrlichiosis, and preliminary studies with the rP140 of *E. canis* suggest that it may be a sensitive and reliable immunodiagnostic antigen (25, 26).

The prior art is deficient in the lack of *Ehrlichia canis*-specific antigen for the immunodiagnosis of canine ehrlichiosis. The present invention fulfills this longstanding need and desire in the art.

SUMMARY OF THE INVENTION

In this study, a new highly immunoreactive *E. canis* protein gene of 1170-bp encoding a protein with predicted molecular mass of 42.6-kD was cloned. The gene was not detected in *E. chaffeensis* DNA, and antibodies against the P43 did not react with *E. chaffeensis* antigen by IFA. The protein was localized to the surface of *E. canis* by immunoelectron microscopy. Use of the rP43 protein for serodiagnosis of canine ehrlichiosis was compared to previously described immunoreactive *E. canis* rP28 and rP140 proteins. *E. canis* rP43 and rP28 were found to be the sensitive and reliable for the serologic diagnosis of canine monocytotrophic ehrlichiosis.

Other and further aspects, features, and advantages of the present invention will be apparent from the following description of the presently preferred embodiments of the invention. These embodiments are given for the purpose of disclosure.

In one embodiment of the current invention, DNA encoding *Ehrlichia canis* immunoreactive surface protein P43 is described. In addition to the DNA sequence described herein, this isolated DNA may also consist of DNA which hybridizes to the P43 DNA and encodes a P43 protein or DNA encoding a P43 protein but differing in codon sequence due to the degeneracy of the genetic code. Preferably, the DNA has the sequence shown in SEQ ID No: 1 and the P43 protein has the amino acid sequence shown in SEQ ID No: 2.

In another embodiment of the instant invention, a vector is provided comprising the P43 DNA and regulatory elements necessary for the expression of the P43 gene in a cell. This vector may be transfected into host cells selected from bacterial cells, mammalian cells, plant cells or insect cells. The bacterial cells may be *E. coli* cells.

In a yet another embodiment of the instant invention, an isolated and purified *Ehrlichia canis* immunoreactive surface protein is provided. This P43 protein may be encoded by the DNA described herein. Alternatively, the protein may be encoded by DNA which hybridizes to the DNA described herein or DNA which differs in nucleotide sequence but encodes the same due to the degeneracy of the genetic code. In a preferred embodiment, the protein has the amino acid sequence shown in SEQ ID No: 2.

In another embodiment of the instant invention, a n antibody may be directed against the P43 protein. In one embodiment, this antibody is a monoclonal antibody.

In yet another embodiment of the instant invention, the P43 protein may be used in the preparation of a vaccine against canine ehrlichiosis.

In a further embodiment of the instant invention, a method of determining whether a dog is infected with *Ehrlichia canis* is provided by testing whether serum from a potentially infected dog reacts to *E. canis* P43 protein. The P43 protein used may be a recombinant P43, and western blot analysis may be used to determine whether the dog's serum reacts to the P43 protein antigen. Since reactivity to P28 is also a reliable marker for *Ehrlichia canis* infection, reaction to both antigens may be used for a conclusive diagnosis.

In yet another embodiment of the instant invention, serodiagnostic kit is provided for determining whether a dog is infected with *Ehrlichia canis*. The kit is comprised immobilized *Ehrlichia canis* antigens (P43, P28 or both), appropriate dilution buffers for dog serum, anti-dog serum second antibody linked to a reporter molecule, appropriate reagents for detection of said reporter molecule. The antigens may be immobilized on membranes or linked to microtiter plates. The reporter molecule may be luciferase, alkaline phosphotase, horseradish peroxidase, β-galactosidase, or a fluorescent label.

In another embodiment of the instant invention, a PCR amplification method is provided for whether a dog has been infected with *Ehrlichia canis*. DNA is extracted from the blood of a potentially infected dog and subjected to PCR amplification with oligonucleotide primers specific for the *E. canis* P43 gene. The resulting PCR amplification products are separated by size by a method such as gel electrophoresis and detection of an appropriately sized product indicates *Ehrlichia canis* infection. Examples of appropriate oligonucleotide primers are SEQ ID No. 9, SEQ ID No. 10, SEQ ID No. 11, and SEQ ID No. 12.

In yet another embodiment of the instant invention, a kit is provided for PCR detection of the P43 gene in dog blood. The kit comprises reagents for DNA extraction from blood, P43-specific oligonucleotides, and reagents for PCR amplification.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the conversion adapters with core annealing sequences which were produced in three reading frames ($A_{1-3}$, $B_{1-3}$, $C_{1-3}$) and used for cloning the *E. canis* p43. The restriction enzymes Hpa I and HinP1 I were used to digest the *E. canis* DNA to produce the same cohesive ends (GC), which were ligated to the conversion adapter. The Eco RI cohesive end allowed direct ligation to the Lambda Zap II vector.

FIG. 2 illustrates the DNA sequence of the 43-kD protein gene of *E. canis*. The primer sequences used to amplify and clone the gene into the prokaryotic expression vector are shown in bold.

DETAILED DESCRIPTION OF THE INVENTION

Figure 3:
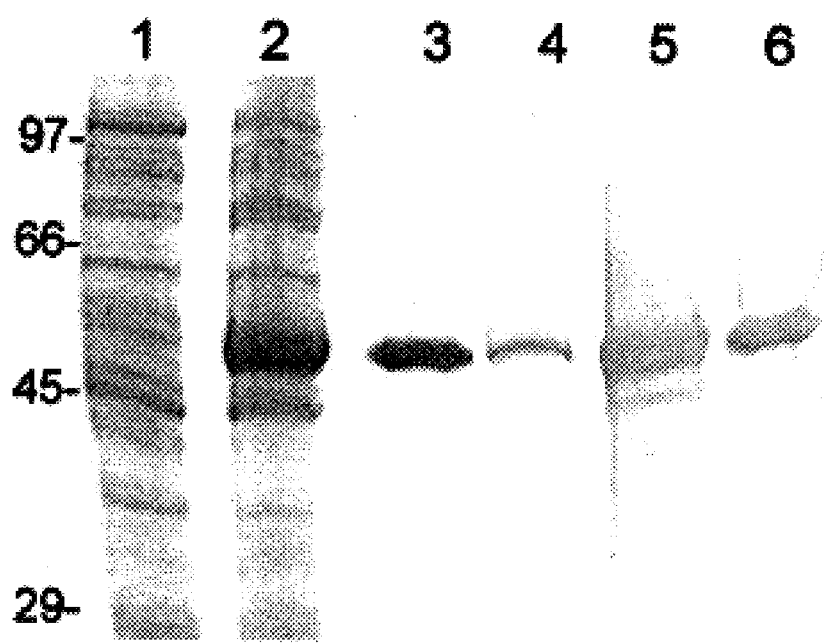
FIG. 3 shows the expression of *E. canis* P43 recombinant protein in *E. coli* BL21 with a 6×histidine fusion tag. Coomassie stained uninduced p43-*E. coli* BL21, p43-*E. coli* induced with IPTG, and purified *E. canis* rP43 are shown in lanes 1–3, respectively. A corresponding Western immunoblot with canine anti-*E. canis* antiserum is shown in lanes 4–6.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acids described herein are preferred to be in the "L" isomeric form. However, residues in the "D" isomeric form can be substituted for any L-amino acid residue, as long as the desired functional property of immunoglobulin binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more deoxyribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "host" is meant to include not only prokaryotes but also eukaryotes such as yeast, plant and animal cells. A recombinant DNA molecule or gene which encodes a protein of the present invention can be used to transform a host using any of the techniques commonly known to those of ordinary skill in the art. Prokaryotic hosts may include *E. coli, S. typhimurium, Serratia marcescens* and *Bacillus subtilis*. Eukaryotic hosts include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

The current invention is directed to DNA encoding *Ehrlichia canis* immunoreactive surface protein P43. Preferably, the DNA has the sequence shown in SEQ ID No: 1 and encodes the P43 protein shown in amino acid sequence SEQ ID No: 2 Alternatively, the DNA may be DNA which hybridizes to SEQ ID No. 1 and encodes a P43 protein or which differs in nucleotide sequence due to the degeneracy of the genetic code.

The instant invention is also directed to a vector comprising the DNA of claim 1 and regulatory elements necessary for expression of the DNA in a cell. This vector may be expressed in a host cell selected from bacterial cells, mammalian cells, plant cells and insect cells. The bacterial cells may be *E. coli* cells.

The instant invention is further directed to isolated and purified *Ehrlichia canis* immunoreactive surface protein P43. Preferably, this protein has the amino acid sequence shown in SEQ ID No:2.

The instant invention is also directed to an antibody directed against the P43 protein. This antibody may be a monoclonal antibody.

The instant invention is further directed to the use of the P43 protein in the preparation of a vaccine against canine ehrlichiosis.

In addition, the instant invention is directed to a method of determining whether a dog is infected with *Ehrlichia canis* by determining whether serum from the dog reacts with *E. canis* P43 protein. The P43 protein used may be from recombinant sources, and western blot analysis may be used to detect the reaction of the serum to the protein. As reaction with previously isolated *E. canis* P28 protein is also reliable marker of *E. canis* infection, diagnosis may consist of detecting immunoreactivity to both the P43 and P28 antigens of *Ehrlichia canis*.

The instant invention is also directed to a serodiagnostic kit for determining whether a dog is infected with *Ehrlichia canis*. The kit comprises immobilized *Ehrlichia canis* antigens (P43, P28 or both), appropriate dilution buffers for dog serum, anti-dog serum second antibody linked to a reporter molecule, appropriate reagents for detection of said reporter molecule. Possible methods of immobilizing the antigens include linkage to membranes or microtiter plates. The reporter molecule may be luciferase, horseradish peroxidase, β-galactosidase, or a fluorescent label.

The instant invention is also directed to a PCR amplification method of determining whether a dog has been infected with *Ehrlichia canis*. DNA is extracted from the blood of a potentially infected dog and subjected to PCR amplification with oligonucleotide primers specific for the *E. canis* P43 gene. The resulting PCR amplification products are separated by size by a method such as gel electrophoresis, and detection of an appropriately sized product indicates *Ehrlichia canis* infection. Examples of appropriate oligonucleotide primers are SEQ ID No. 9, SEQ ID No. 10, SEQ ID No. 11, and SEQ ID No. 12.

The instant invention is also directed to a kit for the PCR detection of the P43 gene and thus *Ehrlichia canis* in dog blood. The kit comprises reagents for DNA extraction from blood, P43 specific oligonucleotides, and reagents for PCR amplification.

The following examples are given for the purpose of illustrating various embodiments of the invention and are not meant to limit the present invention in any fashion.

EXAMPLE 1

Purification of Ehrlichiae

*Ehrlichia canis* Jake strain was isolated by Edward Breitschwerdt and Michael Levy, (College of Veterinary Medicine, North Carolina State University, Raleigh, N.C.). Propagation of ehrlichiae was performed in DH82 cells with Dulbecco modified Eagle medium (DMEM) supplemented with 10% bovine calf serum and 2 mM L-glutamine at 37° C. Intracellular growth in DH82 cells was monitored by presence of *E. canis* morulae using general cytologic staining methods. Cells were harvested when 90–100% of the cells were infected. Cells were harvested and disrupted with a Braun-Sonic 2000 sonicator twice at 40 W for 30 seconds on ice, and ehrlichiae were purified as described previously (20). The lysate was loaded onto discontinuous gradients of 42, 36, and 30% renografin, and centrifuged at 80,000×g for 1 h. Heavy and light bands containing ehrlichiae were collected and washed with sucrose-phosphate-potassium buffer (SPK) [0.2 M sucrose, 0.05 M $KPO_4$, pH 7.4] and pelleted by centrifugation.

EXAMPLE 2

Construction of the *E. canis* Genomic Library

*E. canis* genomic DNA was prepared from purified *E. canis* as previously described (9). The DNA was completely digested with restriction enzymes HinP1 I and Hpa II (10 U of each enzyme for 1 h). The digested *E. canis* DNA fragments were cloned into predigested EcoR I Lambda Zap II vector (Stratagene, La Jolla, Calif.) by using duplex oligonucleotide conversion adapters (BioSynthesis, Lewisville, Tex.) with Hpa II/HinP1 I (GC) and EcoR I (AATT) cohesive ends separated by a 12-bp annealing core as described previously (18) (FIG. 1). Single stranded oligonucleotides with the Hpa II/HinP1 I (strand A) and EcoR I cohesive ends (strand B) were mixed in equal molar concentration (20 μM) in Tris-$MgCl_2$ (25 mM Tris, pH 8.0, 10 mM $MgCl_2$). The mixtures were heated to 95° C. and cooled to room temperature over a 1 hour period to produce the duplex conversion adapter. Efficiency of the adapter duplex formation was determined by acrylamide electrophoresis using a 5% TBE resolving gel. The duplex adapters were produced in three different lengths (A1, A2, A3, B1, B2, B3) to allow gene ligation and expression in three reading frames (FIG. 1). Duplex adapters and restriction enzyme-digested *E. canis* genomic DNA fragments at 10:1 ratio were ligated with 4 U of T4 DNA ligase (Gibco, Grand Island, N.Y.) for 2 h at 14° C., and excess adapter was removed with a PCR purification kit (Qiagen, Valencia, Calif.). The adapter-ligated insert was phosphorylated with 1 U of T4 kinase (New England BioLabs, Beverly, Mass.) for 30 min at 37° C., and the kinase was removed by using a PCR purification kit. The purified *E. canis* DNA-adapter fragments were ligated to the Lambda ZAP II vector by incubation with 2 U of T4 DNA ligase (Gibco) overnight at 14° C. The ligated vector-*E. canis* DNA construct was packaged for 1.75 h at room temperature using Gigapack III gold packaging extract (Stratagene) to obtain the packaged phage. A titration procedure was performed to determine plaque forming units of the phage.

EXAMPLE 3

Selection of *E. canis* Recombinants

Anti-*E. canis* sera from 6 naturally infected dogs diagnosed at Louisiana State University, Baton Rouge were pooled and absorbed with XL-1 Blue *E. coli* to reduce background signal. The immunoreactivity of the pooled sera was determined by Western immunoblot with *E. canis* antigen. Packaged Lambda ZAP II phage were incubated with *E. coli* XL-1 Blue (600 μl at $OD_{600}$ of 0.5) at the appropriate dilution for 15 min. The bacteria/phage mixture was added to 7 ml of melted NZY agar with isopropyl-1-thio-β-D-galactopyranoside (IPTG) and 5-bromo-4-chloro-3-indoyl-β-D-galactopyranoside (X-gal), cooled to 48° C. and plated on NZY agar plates (150 mm). A nitrocellulose membrane soaked in 10 mM IPTG for 30 min was placed on the solidified agar surface. The plates were incubated overnight at 37° C. for 15 hours. Nitrocellulose membranes were removed and blocked with 2% nonfat milk in Tris-buffered saline (TBS, pH 7.4) for 1 h and incubated with the pooled canine anti-*E. canis* serum diluted 1:10,000 in blocking buffer for 2 hour. Membranes were washed and incubated with an affinity purified goat anti-canine 1 gG (H+L chain) alkaline phosphatase-labeled conjugate (Kirkegaard & Perry Laboratories, Gaithersburg, Md.) at 1:5000 for 1 hour, and after washing again, bound antibody was detected with 5-bromo-4-chloro-3-indolyl phosphate-nitroblue tetrazolium (BCIP/NBT). Plaques corresponding to positive reactions with *E. canis* antisera were purified by a single-plaque isolation and stored in SM buffer (0.1 M NaCl, 10 mM Tris, pH 7.5, 10 mM $MgSO_4$ and 2% gelatin) with chloroform. A second antibody screening on the isolated plaques was performed to confirm antibody reactivity and plaque purity.

EXAMPLE 4

Recombinant Clone Excision and Plasmid Recovery

The recombinant phage were excised by incubation with XL-1 Blue MRF' *E. coli* and ExAssist helper phage (Stratagene, La Jolla, Calif.) in LB broth at 37° C. overnight. The pBluescript plasmids were recovered by incubating the excised pBluescript phage with SOLAR cells (Stratagene) and plating the mixture on LB-ampicillin agar plates. Plasmids recovered from resistant colonies were analyzed by digestion with EcoR I corresponding to the conversion adapter/vector restriction site to confirm the presence of an insert. Inserts were sequenced with an ABI Prism 377 DNA Sequencer (Perkin-Elmer Applied Biosystems, Foster City, Calif.). Colonies that contained the plasmids with insert were recovered and frozen in glycerol at −80° C. for long term storage.

EXAMPLE 5

Cloning, Expression, and Immunoreactivity of Recombinant *E. canis* P43

A segment representing 95% of the p43 gene was amplified by PCR and cloned directly into pCR T7/CT TOPO TA expression vector (Invitrogen, Carlsbad, Calif.) designed to produce proteins with a native N-terminus and a carboxy terminal polyhistidine region for purification. Forward primer ECa43BADf [5'-ATG TCA GAT CCA AAA CAA GGT G-3' (SEQ ID No. 9)] and reverse primer ECa43BADr [5'-TCC ATC TAC AAG TCC AAA ATC TAA-3' (SEQ ID No. 10), designed to produce a 1113-bp PCR product in the correct frame for expression, were used to amplify the entire gene, excluding the last 57-bp of the open reading frame (ORF) on the carboxy terminal. The cloned p43 gene was transformed into TOP10 *E. coli,* and positive transformants were screened for the presence of plasmid with the appropriate insert. Transformants containing the plasmid with insert were sequenced to confirm the reading frame and orientation of the p43 gene. Plasmids containing the proper insert were used to transform BL21 (DE3) pLysS *E. coli* for protein expression. Expression of P43 was performed by induction with 0.5 mM IPTG for 4 hours. Recombinant P43 was purified by lysing BL21 *E. coli* cells under denaturing conditions (8 M urea; 0.1 M $NaH_2PO_4$; 0.01 Tris-Cl; pH 8.0) for 1 hour. The lysate was clarified by centrifugation at 10,000×g for 20–30 min., and the supernatant was loaded on an equilibrated nickel-nitriloacetic acid (Ni-NTA) spin column (Qiagen, Valencia, Calif.). The bound recombinant protein was washed three times with the denaturing buffer (pH 6.3), and eluted with denaturing buffer (pH 4.5). Purified recombinant protein was dialyzed against ultrapure $H_2O$ for 30 min in microdialyzers (Pierce, Rockford, Ill.). The expressed recombinant E. canis P43 was subjected to SDS-polyacrylamide gel electrophoresis (SDS-PAGE) as described previously and transferred to pure nitrocellulose using a semidry electroblotting cell (Bio-Rad, Hercules, Calif.). The membrane was blocked for 1 hr in 1% nonfat milk and incubated with canine anti-E. canis antibody diluted 1:1000 or anti-mouse r P43 for 1 hour. The membrane was incubated with an affinity-purified alkaline phosphatase-labeled anti-canine 1 gG (H+L chain) or anti-mouse IgG conjugate (1:5000) (Kirkegaard & Perry Laboratories), and bound antibody was detected with BCIP/NBT substrate (Kirkgaard & Perry Laboratories).

EXAMPLE 6
Southern Blotting

A digoxigenin (DIG) labeled DNA probe was produced by PCR amplification of the p43 gene with primers p43-274f [5'-GAA CCG AAA GTA GAA GAT GAT GAA GA-3' (SEQ ID No. 11)] and p43-1185r [5'-TAA GTT AAC AGG TGG CAA ATG-3' (SEQ ID No. 12)] using DIG-labeled deoxynucleotides. A single product 911-bp was visualized on an ethidium-bromide-stained agarose gel. Removal of excess dNTPs and primers from the PCR-produced P43 probe was performed using a QIAquick PCR purification kit (Qiagen). E. canis and E. chaffeensis genomic DNA was quantified spectrophotometrically at $A_{260/280}$, and 0.5 µg of the DNA was digested overnight with Ase I. The digested DNA was separated on a 1.3% agarose gel with DIG-labeled molecular mass markers (DNA Molecular Weight marker II, Roche Molecular Biochemicals, Indianapolis, Ind.) and transferred to a nitrocellulose membrane by capillary transfer. The membrane-bound DNA was crosslinked by ultraviolet exposure, and the membrane was blocked with DIG Easy Hyb buffer (Roche) for 30 min. The denatured p43 DIG-labeled probe was diluted in 7 ml of DIG Easy Hyb buffer at a concentration of 20 ng/ml and hybridized with the membrane overnight at 39° C. The membrane was washed twice in 2×SSC/0.1% SDS at 65° C. for 5 min each, and 0.5×SSC/0.1% SDS for 15 min. The membrane was incubated in blocking buffer (100 mM maleic acid, 150 mM NaCl; pH 7.5; containing 1% blocking reagent), then washed and incubated for 30 min with alkaline phosphatase-labeled anti-DIG antibody diluted 1:5000. The bound DIG-labeled p43 probe was detected with BCIP/NBT substrate (Kirkegaard & Perry Laboratories).

EXAMPLE 7
Immunelectron Microscopy

A suspension of purified E. canis organisms was placed on Formvar-carbon coated nickel grids and incubated with mouse anti-recombinant P43 polyclonal antibodies (diluted 1:10 and 1:100 in blocking buffer, 1% bovine serum albumin in PBS) followed by goat anti-mouse IgG+IgM (H+L) labeled with 10 nm colloidal gold particles (AutoProbe EM GAM IgG+IgM G10, RPN431; Amersham Life Science, Arlington Heights, Ill.) diluted 1:20 in blocking buffer. After washing, the grids were fixed in 2% aqueous glutaraldehyde, washed again, and negatively stained with 2% phosphotungstic acid adjusted to pH 6.8 with 1N KOH. They were examined in Philips 201 electron microscope at 60 kV with instrumental magnifications×20,000 and ×30,000.

EXAMPLE 8
Dog Sera

Forty two sera from dogs of various breeds suspected of having canine ehrlichiosis based on clinical signs and/or hematologic abnormalities were submitted to the Louisiana Veterinary Medical Diagnostic Laboratory from veterinarians statewide (Table 1). Six E. canis IFA positive sera from dogs naturally infected in North Carolina, Virginia and California were provided from North Carolina State University, College of Veterinary Medicine (Table 1). Negative control serum was obtained from 15 healthy laboratory-reared beagles (Marshall Farms USA, Inc., North Rose, N.Y.), 1 to 2 years of age, housed in indoor kennels.

TABLE 1

Summary of historical and hematological abnormalities of 42 dogs suspected of having canine monocytotropic ehrlichiosis

| Dog | Age | Sex | Breed | Clinical History | Hematologic Abnormalities |
|---|---|---|---|---|---|
| 1 | 12 | M | Skye Terrier | Lethargy, anorexia, labored | Thrombocytopenia, anemia |
| 2 | 5 | M | Catohoula Curr X | ND | ND |
| 3 | 11 | M/N | Mixed | Chronic uveitis, corneal edema | ND |
| 4 | 11 | F/S | Mixed | ND | ND |
| 5 | 5 | M | Catahoula Curr | Tick bites | Thrombocytopenia, Leukopenia |
| 6 | 9 | M/N | Mixed | ND | ND |
| 7 | 3 | M | Mixed | Chronic lameness | ND |
| 8 | 7 | M/N | Boxer X | ND | ND |
| 9 | 7 | F/S | Chow/Rott X | Chronic nephritis, melena, wt. loss | ND |
| 10 | 7 | ND | CA Red Tick Hound | ND | TP > 10.0, Hypergammaglobulimemia |
| 11 | 5.5 | M | Shitzu | Lymphadenopathy, skin hemorage | ND |
| 12 | 1.5 | F/S | Golden Retriever | Scleral injection, lethargy | Lymphopenia |
| 13 | ND | F/S | Mixed | Excessive bleedbleeding during spaying | Thrombocytopenia |
| 14 | 11 | F/S | Heeler | Lymphadenitis, lameness | Thrombocytopenia, anemia |
| 15 | 9 | F/S | Labrador | History of ehrlichosis | ND |
| 16 | 4 | M/N | Great Dane | Non regenerative anemia, | ND |
| 17 | 2 | F | Mixed | Non responder | Anemia, thromb, hypoalbum, hyperglob |
| 18 | 7 | M | Mixed | Profuse epistaxis | Anemia, thromb, hyperglob. |
| 19 | 7 | M | Mixed | Anorexic, cough, bleeding ulcer | Anemia, neutropenia, thrombo, nephropath |
| 20 | 4 | M | Boykin Spaniel | Anterior uveitis, acute renal failure | Anemia, thrombocytopenia, neutrophilia |
| 21 | 7 | F | Bulldog | Keratoconjunctivitis sicca, fever | Anemia, thrombo, hypoalbum, hyperglob |
| 22 | 10 | F | Golden Retriever | Non responder | ND |
| 23 | 5 mth | M | Schnauzer | Healthy | Thrombocytopenia |
| 24 | ND | M/N | Belgian Tervuren | ND | ND |
| 25 | 1.5 | M/N | Brittany | Petechiae on mucous membranes, | ND |
| 26 | 8 | F/S | Collie | ND | ND |
| 27 | ND | ND | ND | ND | ND |
| 28 | 4 | M | Chow Mix | Severe uveitis, increased blood | ND |
| 29 | 3 | F | Catahoula Curr X | Lethargic, tick history | ND |

TABLE 1-continued

Summary of historical and hematological abnormalities of 42 dogs suspected of having canine monocytotropic ehrlichiosis

| Dog | Age | Sex | Breed | Clinical History | Hematologic Abnormalities |
|---|---|---|---|---|---|
| 30 | 10 | M | Mixed | Bleeding from venipuncture | Thrombocyotopenia |
| 31 | 3.5 | M | Labrador | Febrile, lame, limb edema | Thrombocyotopenia |
| 32 | 6 | F | Fox Terrier | Lethargy, norm temp, flex/ext pain | ND |
| 33 | 12 | M | Labrador | ND | ND |
| 34 | 4 | M | German Shep | Weight loss, fever | Neutrophil leukocytosis |
| 35 | 3 | M/N | Poodle | Non specific clincal signs | Thrombocyotopenia |
| 36 | 7 | M | Labrador | Lame following exercise-recovers | ND |
| 37 | 7 mths | M | Mixed | Lethargic, anorexia, febrile | Thrombcyotopenia, leukopenia |
| 38 | 9 | M | German Shep | History of splenomegaly | ND |
| 39 | 2 | M | Pit Bull | ND | Thrombocyotopenia |
| 40 | 4 | M | Mixed | No signs | Thrombocyotopenia |
| 41 | 10 | F | Sheltie | Healthy | ND |
| 42 | 1 | M/N | Mixed | Recur fever, gastritis, splenomegaly | Leukocytosis |

EXAMPLE 9
IFA

Antigen slides were prepared using *E. canis* Louisiana strain-infected dog bone marrow cells as described previously (6). The infected cells were washed in PBS and resuspended in 10 ml of PBS with 0.01% bovine albumin. Ten microliters of antigen were applied to each well of 12-well slides. The slides were air-dried and acetone fixed for 10 min. Serial two-fold dilutions of dog sera were prepared in PBS from an initial dilution of 1:40. Ten microliters of the diluted serum were added to each well. Slides were incubated at 37° C. for 30 min, washed twice in PBS and air-dried. An affinity purified fluorescein isothiocyanate (FITC)-conjugated goat anti-canine IgG (H+L chain) antibody (Kirkegaard & Perry Laboratories) diluted 1:50 was added to each well and incubated for 30 min. Slides were washed, coverslipped, and examined using an UV microscope with filters for fluorescein. An antibody titer of 1:40 or greater was considered positive.

To demonstrate the specificity or cross reactivity of polyclonal antibodies produced against the rP43, an IFA using anti-recombinant P43 antisera was performed with *E. canis* and *E. chaffeensis* antigen slides. Antigen slides were incubated with anti-P43 polyclonal serum diluted 1:100. The slides were washed and incubated with an anti-mouse IgG FITC-labeled antibody and examined as described above.

EXAMPLE 10
Recombinant Proteins

The *E. canis* rP140 and rP28 have been previously described (10, 23, 26). The *E. canis* rP140 contained 78% of the ORF, primarily the repeat region, and the *E. canis* rP28 included the entire ORF. The rP43 expressed protein included 95% of the ORF, excluding the last 19 C-terminus amino acids of the protein described in this report.

EXAMPLE 11
Western Blotting of Clinical Sera

The recombinant proteins were separated on a preparative 12% sodium dodecyl sulfate (SDS) polyacrylamide slab minigel under denaturing conditions. The proteins were transferred to pure nitrocellulose membrane (Schleicher & Schuell, Keene, NH, 0.45 μm) by using a Trans-Blot SD Transfer Cell (Bio-Rad) at 15 V for 30 min. The protein transfer was monitored by staining membranes with Ponceau S. The position of each recombinant protein was recorded, and the membranes were blocked in 2% non-fat milk. The membranes were placed in a Mini-Protein II Multiscreen Apparatus (Bio-Rad), with a 1:100 dilution of each dog serum and incubated for 1 hour with continuous orbital rocking. The membrane was removed and washed three times with 0.1 M Tris-buffered saline (TBS) (pH 7.4) and Tween 20 (0.02%). The membranes were then incubated with a secondary affinity purified, alkaline phosphatase-labeled anti-dog IgG (H+L chain) conjugate (Kirkegaard & Perry Laboratories) diluted 1:5000 for 1 h with continuous agitation. After washing, bound antibody was visualized with BCIP/NBT substrate

EXAMPLE 12
p43 Gene Sequence

Twelve clones reactive with the pooled anti-*E. canis* dog sera were digested with Eco RI to determine if the clones contained *E. canis* DNA inserts. Four clones ($4_1, 5_2, 7_2, 8_4$) had a 2.9 kb insert as identified by agarose gel electrophoresis. These four clones were selected for further sequencing with an ABI Prism 377 DNA Sequencer (Perkin-Elmer Applied Biosystems, Foster City, Calif.) and were determined to be identical. One complete and 2 incomplete open reading frames were identified in these clones. The complete open reading frame was 1170-bp in length encoding a predicted protein of 390 amino acids with a predicted molecular mass of 42.6-kD (FIG. 1). There were no signal sequences identified, and the protein was predicted to be cytoplasmic. A Blast search revealed that the P43 amino acid sequence exhibited significant similarity (45%) with an 88 amino acid region from the human granulocytic ehrlichiosis (HGE) agent P160 protein. An incomplete open reading frame 5' of the p43 gene had significant homology (56%) with the deoxyguanosine triphosphate triphosphohydrolase of *Rickettsia prowazekii*. The incomplete open reading frame 3' of the p43 gene had homology with numerous ankyrin proteins. The GenBank accession number for the nucleic acid and amino acid sequences of the *E. canis* p43 gene described in this patent is AF252298.

EXAMPLE 13
Cloning, Expression, and Immunoreactivity of the p43 Gene

Figure 4:
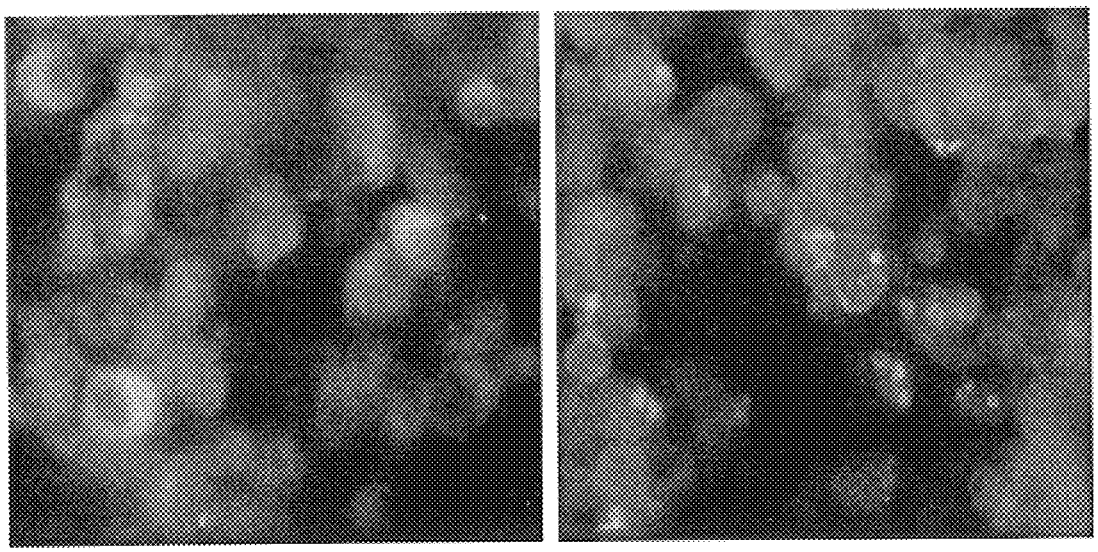
FIG. 4 shows reaction of anti-rP43 with *E. canis* (right) and *E. chaffeensis* (left) infected DH82 cells by IFA, demonstrating reactivity only with the *E. canis* antigen.

An 1113-bp product was amplified from genomic *E. canis* DNA using p43BADf and p43BADr and cloned directly into a prokaryotic expression vector (pCRT7/CT, Invitrogen). The rP43 (95% ORF) was expressed in *E. coli*, and it exhibited a molecular mass of approximately 50-kD including the C-terminal fusion tag (5-kD) (FIG. 3). The molecular mass of the expressed protein (45-kD) was slightly larger than the predicted mass after subtraction of the C-terminal fusion tag (5-kD). The recombinant expressed protein reacted with anti-*E. canis* antiserum from an infected dog and the anti-rP43 antibody produced in a mouse (FIG. 3). The anti-rP43 did not react with native *E. canis* antigen separated by SDS-PAGE, but did react with *E. canis* infected DH82 cells by IFA (FIG. 4). The polyclonal anti-rP43 did not react with *E. chaffeensis* infected DH82 cells by IFA.

EXAMPLE 15
Immunoelectron Microscopy

Figure 5:
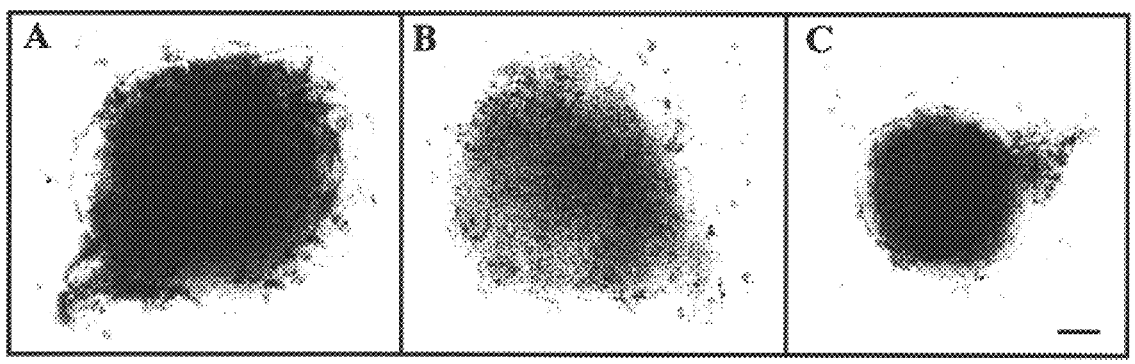
FIG. 5 shows an immunoelectron photomicrograph of *E. canis* reticulate forms (A and B) and dense core form (C) negatively stained with 2% phosphotungstic acid and reacted with mouse anti-rP43 followed by colloidal gold-labeled anti-mouse IgG (H+L). The P43 is seen on the outer membrane of *E. canis* verifying its surface location. Bar=1 μm.

The P43 was identified on the outer membrane of negatively stained E. canis organisms (FIG. 5), indicating that the P43 is a surface exposed protein.

EXAMPLE 16
Southern Blotting

Figure 6:
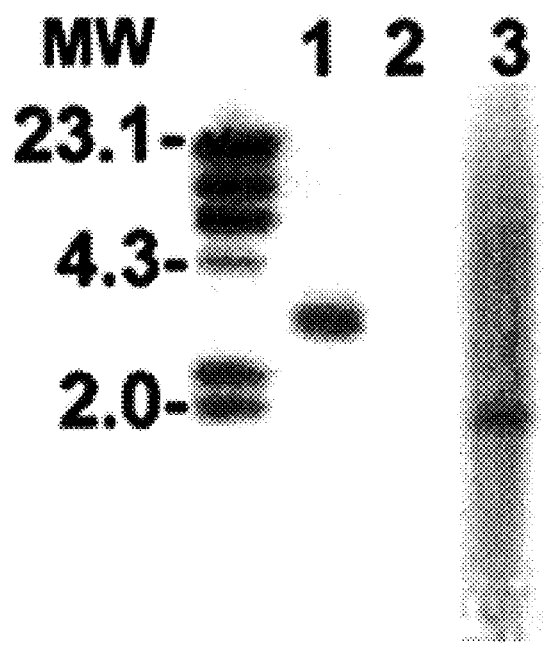
FIG. 6 shows southern blot analysis of *E. canis* and *E. chaffeensis* DNA (0.5 μg) using a 911-bp DIG-labeled p43 gene probe. The *E. canis* p43 hybridized with a single band in the genomic DNA of *E. canis* digested with Ase I (Lane 2), but *E. chaffeensis* DNA did not hybridize with the gene probe (Lane 3). Lane 1 shows a digoxigenin-labeled DNA marker (in kilobases).

To determine if a homologous gene was present in E. chaffeensis, a Southern blot was performed with a DIG-labeled DNA probe. The p43 gene was identified in an approximately 3-kb fragment of Ase I-digested E. canis genomic DNA, but the probe did not hybridize with E. chaffeensis genomic DNA digested similarly (FIG. 6), indicating that a closely related homologous gene was not detected in E. chaffeensis. Further attempts using PCR with four different primer pairs derived from the E. canis p43 gene sequence failed to identify a p43 homolog in E. chaffeensis.

EXAMPLE 17
Serodiagnosis by IFA and Recombinant Proteins

Figure 7:
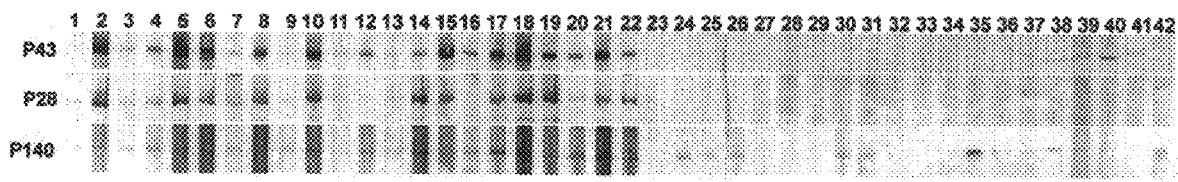
FIG. 7 shows protein immunoblotting of suspect canine ehrlichiosis cases with antibodies against recombinant *E. canis* P43, P28, and P140.

The 42 cases clinically suspected to be canine ehrlichiosis when evaluated by IFA detected 22 seropositive cases with titers ranging from 40 to >40960 (Table 2 and FIG. 7). Approximately half of the 42 samples had titers greater than 80, and the other half had titers of 40 or less, which provided the appropriate samples for evaluation of overall sensitivity of the IFA and recombinant proteins. Twenty of the 42 samples were negative by IFA at 1:40. The recombinant E. canis rP43 had the best correlation with positive IFA samples at 100% sensitivity, followed by the P28 (96%) and the r140 (96%). All samples with IFA titers of 80 had 100% positive correlation with the all of the recombinant antigens, and the density of the reaction by Western immunoblot appeared to be proportional to the IFA titer (FIG. 7). The rP43 and rP28 exhibited the best combination of sensitivity and specificity, and the rP140 reacted nonspecifically with several IFA negative sera. The observation that three dogs which were IFA negative for E. canis were weakly positive to the rP43 antigen suggests that this antigen may be more sensitive than the IFA, rather than less specific. To confirm the specificity, 15 laboratory-reared dogs without a prior history of canine ehrlichiosis were tested, and all were negative by IFA. Although none of their sera reacted with the rP43 or the rP28, the sera of eight of these dogs reacted with the rP140 (not shown).

TABLE 2

Reaction of suspect canine ehrlichiosis sera by IFA and with recombinant E. canis proteins by Western immunoblot

| | | E. canis Protein | | |
|---|---|---|---|---|
| Dog no. | IFA titer | P43 | P140 | P28 |
| 1 | 160 | + | + | + |
| 2 | >2560 | + | + | + |
| 3 | 80 | + | + | + |
| 4 | 2560 | + | + | + |
| 5 | >2560 | + | + | + |
| 6 | 2560 | + | + | + |
| 7 | 640 | + | + | + |
| 8 | >2560 | + | + | + |
| 9 | 80 | + | + | + |
| 10 | >40960 | + | + | + |
| 11 | 40 | + | + | + |
| 12 | 1280 | + | + | + |
| 13 | 160 | + | + | + |
| 14 | 10240 | + | + | + |
| 15 | 20480 | + | + | + |
| 16 | 640 | + | + | − |
| 17 | >10240 | + | + | + |
| 18 | >10240 | + | + | + |
| 19 | 2560 | + | + | + |
| 20 | 5120 | + | + | + |
| 21 | 10240 | + | + | + |
| 22 | 5120 | + | + | + |
| 23 | <40 | − | − | − |
| 24 | <40 | − | + | − |
| 25 | <40 | − | + | − |
| 26 | <40 | − | + | − |
| 27 | <40 | − | − | − |
| 28 | <40 | − | − | − |
| 29 | <40 | − | + | − |
| 30 | <40 | − | + | − |
| 31 | <40 | + | + | − |
| 32 | <40 | − | + | − |
| 33 | <40 | − | − | − |
| 34 | <40 | − | − | − |
| 35 | <40 | − | + | − |
| 36 | <40 | − | + | − |
| 37 | <40 | − | + | − |
| 38 | <40 | − | + | − |
| 39 | <40 | + | + | − |
| 40 | <40 | + | − | − |
| 41 | <40 | − | − | − |
| 42 | <40 | − | + | − |

EXAMPLE 18
Discussion

The immunoreactivity and potential use of the E. canis rp140 and rP28 as serodiagnostic antigens has been previously demonstratred (10, 26). A new immunoreactive protein of E. canis usefull for serodiagnosis has been identified herein. Reaction with antibodies against rP43 had a 100% correlation with samples having an IFA titer >40 and did react with several samples with IFA titers of <40. The weak reactivity of several IFA negative samples with the rP43 suggests that it may be more sensitive; however the paired serum samples were not available to confirm disease in these dogs. P43 is strongly immunoreactive, and the molecular mass coincides with other ehrlichial proteins observed by Western blot that are immunodominant and cross-reactive between species. This led to speculation that a homologous p43 gene was present in E. chaffeensis. Hence, an attempt was made to identify a homologous gene in E. chaffeensis by Southern blot and PCR, but no homologous gene was detected. In addition, anti-recombinant P43 polyclonal antibody strongly reacted with E. canis antigen by IFA, but not with E. chaffeensis antigen. This evidence suggests that this protein may be antigenically unique to E. canis, and may not be the cross reactive antigen observed by Western immunoblot of E. chaffeensis antigen.

The absence of a detectable p43 gene copy in the E. chaffeensis genome and of cross reactive antibodies against the protein with E. chaffeensis antigens suggests that it could potentially be used for differentiation of infections with E. canis and E. chaffeensis in dogs or humans. The fact that all IFA positive sera with titers >80 reacted with this apparently species-specific protein suggests that these dogs were infected with E. canis. However, dog 20 was PCR positive on multiple occasions for E. chaffeensis. Conversely, the P28 would not be useful for such differential diagnosis, as cross reactivity between the P28 proteins of *E. canis* and *E. chaffeensis* is well documented (1, 2).

P43 was found on the outer membrane of *E. canis* stained with anti-rP43 by immunoelectron microscopy. The high immunoreactivity of this protein supports this finding. Other highly immunoreactive proteins have been localized to the surface of *E. chaffeensis* (3, 15, 21). The apparent surface location of the P43 suggests a possible role as an adhesin.

The *E. canis* P140 is similar to the *E. chaffeensis* P120 in that both have tandem repeat units and both are glycosylated (12). The proteins are homologous, but the homology occurs primarily in the N-terminus region upstream of the repeat regions. However, small homologous serine-rich motifs have been identified in the repeat regions (12). Antibodies produced against the two recombinant proteins do not cross react (12), and probes designed from each gene did not hybridize in Southern blots with heterologous ehrlichial genomic DNA (26). It was previously reported that the glycosylated P120 of *E. chaffeensis* was specific for diagnosis of HME and IFA negative human sera did not react with the rP120 (22). The reactivity of the rP140 with the *E. canis* IFA negative sera of suspect cases as well as the IFA-negative laboratory reared dogs suggests that nonspecific cross reactive antibodies may be involved. One explanation could be the presence of natural antibodies directed at the carbohydrate glycans attached to this protein. Natural antibodies directed at carbohydrates such as those found on red blood cells (blood group antigens) and endothelial cells (hyperacute organ rejection) are believed to be elicited in response to carbohydrate epitopes displayed by microorganisms and parasites (5). Galactose-α-1,3-galactose is a major epitope of natural antibodies that is well recognized in humans (4). Although little is known about natural antibodies in dogs, there are seven major blood group antigens, suggesting that a wide variety of natural antibodies are present in dogs. The low specificity of the *E. canis* rP140 in dogs is likely due to unique natural antibodies against specific carbohydrate epitopes present on the rP140 of *E. canis* and the rP120 of *E. chaffeensis* in some dogs. The specificity of natural antibodies varies among animals and humans, and thus may explain the reactions of the *E. canis* rP140 observed in dogs, in contrast to the specificity observed using human sera against the similarly glycosylated rP120 of *E. chaffeensis*.

*E. canis* P28 is conserved among geographically separate strains (10, 11). The conservation of this major outer membrane protein among *E. canis* strains certainly makes it an attractive serodiagnostic candidate antigen. In this study, the *E. canis* P28 reacted with 96% of the canine sera with an IFA titer (40). The immunoreactivity of this protein with clinical samples from dogs appears to be much better than the reactivity of the *E. chaffeensis* P28 with human sera. The rP28 of *E. chaffeensis* has proven to be a poor serodiagnostic antigen (25), which is probably related to the diversity of the gene encoding this protein among different strains of *E. chaffeensis* (27). The conservation of *E. canis* p28 gene may explain why the *E. canis* rP28 correlates better with the IFA than does the *E. chaffeensis* rP28. The *E. canis* rP28 appeared to be less reactive than the rP43 when the intensity of the reaction on Western immunoblots was compared. Recent reports have demonstrated that *Anaplasma marginale* expresses unique msp2 genes in the tick salivary gland, and these antigenically distinct msp2 proteins are the first variants expressed during acute rickettsemia after transmission to the vertebrate host (17). Similar expression of unique variant *E. canis* p28 genes in the tick salivary gland, and expression of these unique variants in the vertebrate host after transmission may occur. Thus any P28 used for serodiagnosis that is not transmitted by the arthropod host and expressed in the vertebrate host could potentially be less sensitive at detecting acute phase antibodies.

The possibility of that some of these dogs were infected with *E. ewingii* does exist. It has been reported that sera from dogs infected with *E. ewingii* do not cross react with the P28 proteins of *E. canis* or *E. chaffeensis* (16). Therefore the single case in this study in which there is reactivity with the P43 and P140, but not the P28 could possibly be an *E. ewingii* infection. It is not clear if the *E. canis* P43 and P140 cross-react with antibodies in sera from *E. ewingii* infected dogs, although proteins with molecular masses of 43–47-kD have demonstrated some cross reactivity.

A wide range of antibody titers using the recombinant proteins to determine possible differences in diagnostic sensitivity compared to IFA were evaluated. In these cases submitted for ehrlichiosis testing, several dogs with clinical signs associated with the disease were IFA negative, but reacted positively with the rP43. The reactivity of three IFA negative samples with the rP43 suggests that the recombinant proteins could be more sensitive than the IFA for serodiagnosis. The possibility of cross reactivity of the rP43 elicited by antigens of an unknown agent may exist, but further testing with acute phase and convalescent sera from suspect cases would be necessary to provide the information required to confirm the specificity. It is suggested by this study that low antibody titers may be more difficult to detect with the IFA method. Other factors that may also contribute to variations in IFA results include subjectivity of the endpoint as determined by various readers, differences in antigen production, reagents, and assay conditions. The rP140 appears to be especially sensitive at detecting low antibody titers, which would be particularly important for detecting early *E. canis* infections, considering the best prognosis correlates with early treatment. The use of recombinant proteins for diagnosis of *E. canis* infections would be advantageous to assume greater consistency of the antigen and elimination of test subjectivity.

The following references were cited herein:
1. Chen, S. M., L. C. Cullman, and D. H. Walker. 1997. Western immunoblotting analysis of the antibody responses of patients with human monocytotropic ehrlichiosis to different strains of *Ehrlichia chaffeensis* and *Ehrlichia canis*. Clin. Diagn. Lab. Immunol. 4:731–735.
2. Chen, S. M., J. S. Dumler, H. M. Feng, and D. H. Walker. 1994. Identification of the antigenic constituents of *Ehrlichia chaffeensis*. Am. J. Trop. Med. Hyg. 50:52–58.
3. Chen, S. M., V. L. Popov, H. M. Feng, and D. H. Walker. 1996. Analysis and ultrastructural localization of *Ehrlichia chaffeensis* proteins with monoclonal antibodies. Am. J. Trop. Med. Hyg. 54:405–412.
4. Galili, U., B. A. Macher, J. Buehler, and S. B. Shohet. 1985. Human natural anti-alpha-galactosyl IgG. II. The specific recognition of alpha (1–3)-linked galactose residues. J. Exp. Med. 162:573–582.
5. Galili, U., R. E. Mandrell, R. M. Hamadeh, S. B. Shohet, and J. M. Griffiss. 1988. Interaction between human natural anti-alpha-galactosyl immunoglobulin G and bacteria of the human flora. Infect. Immun. 56:1730–1737.
6. Gaunt, S. D., R. E. Corstvet, C. M. Berry, and B. Brennan. 1996. Isolation of *Ehrlichia canis* from dogs following subcutaneous inoculation. J. Clin. Microbiol. 34:1429–1432.
7. Harrus, S., T. Waner, I. Aizenberg, J. E. Foley, A. M. Poland, and H. Bark. 1998. Amplification of ehrlichial DNA from dogs 34 months after infection with *Ehrlichia canis*. J. Clin. Microbiol. 36:73–76.
8. Huxsoll, D. L., P. K. Hildebrandt, and R. M. Nims. 1970. Tropical canine pancytopenia. J. Am. Vet. Med. Assoc. 157:1627–1632.

9. McBride, J. W., R. E. Corstvet, S. D. Gaunt, J. Chinsangaram, G. Y. Akita, and B. I. Osburn. 1996. PCR detection of acute *Ehrlichia canis* infection in dogs. J. Vet. Diagn. Invest. 8:441–447.
10. McBride, J. W., X. J. Yu, and D. H. Walker. 1999. Molecular cloning of the gene for a conserved major immunoreactive 28-kilodalton protein of *Ehrlichia canis*: a potential serodiagnostic antigen. Clin. Diag. Lab. Immunol. 6:392–399.
11. McBride, J. W., X. J. Yu, and D. H. Walker. 2000. A conserved, transcriptionally active p28 multigene locus of *Ehrlichia canis*. Gene. (Submitted)
12. McBride, J. W., X. J. Yu, and D. H. Walker. 2000. Glycosylation of homologous immunodominant proteins of *Ehrlichia chaffeensis* and *E. canis*. Infect. Immun. 68:13–18.
13. Nyindo, M. B., M. Ristic, D. L. Huxsoll, and A. R. Smith. 1971. Tropical canine pancytopenia: in vitro cultivation of the causative agent—*Ehrlichia canis*. Am. J. Vet. Res. 32:1651–1658.
14. Ohashi, N., A. Unver, N. Zhi, and Y. Rikihisa. 1998. Cloning and characterization of multigenes encoding the immunodominant 30-kilodalton major outer membrane proteins of *Ehrlichia canis* and application of the recombinant protein for serodiagnosis. J. Clin. Microbiol. 36:2671–2680.
15. Ohashi, N., N. Zhi, Y. Zhang, and Y. Rikihisa. 1998. Immunodominant major outer membrane proteins of *Ehrlichia chaffeensis* are encoded by a polymorphic multigene family. Infect. Immun. 66:132–139.
16. Rikihisa, Y., S. A. Ewing, and J. C. Fox. 1994. Western immunoblot analysis of *Ehrlichia chaffeensis, E. canis,* or *E. ewingii* infections in dogs and humans. J. Clin. Microbiol. 32:2107–2112.
17. Rurangirwa, F. R., D. Stiller, D. M. French, and G. H. Palmer. 1999. Restriction of major surface protein 2 (MSP2) variants during tick transmission of the ehrlichia *Anaplasma marginale*. Proceed. Nat. Acad. Sci. 96:3171–3176.
18. Stover, C. K., M. H. Vodkin, and E. V. Oaks. 1997. Use of conversion adaptors to clone antigen genes in λgt11. Anal. Biochem. 163:398–407.
19. Troy, G. C. and S. D. Forrester. 1990. Canine ehrlichiosis, p. 404–418. In C. E. Green (ed.), Infectious diseases of the dog and cat. W.B. Sauders Co., Philadelphia.
20. Weiss, E., J. C. Coolbaugh, and J. C. Williams. 1975. Separation of viable *Rickettsia typhi* from yolk sac and L cell host components by renografin density gradient centrifugation. Appl. Microbiol 30:456–463.
21. Yu, X., P. Brouqui, J. S. Dumler, and D. Raoult. 1993. Detection of *Ehrlichia chaffeensis* in human tissue by using a species-specific monoclonal antibody. J. Clin. Microbiol. 31:3284–3288.
22. Yu, X. J., P. Crocquet-Valdes, L. C. Cullman, V. L. Popov, and D. H. Walker. 1999. Comparison of *Ehrlichia chaffeensis* recombinant proteins for diagnosis of human monocytotropic erhlichiosis. J. Clin. Microbiol. 37:2568–2575.
23. Yu, X. J., P. Crocquet-Valdes, L. C. Cullman, and D. H. Walker. 1996. The recombinant 120-kilodalton protein of *Ehrlichia chaffeensis,* a potential diagnostic tool. J. Clin. Microbiol. 34:2853–2855.
24. Yu, X. J., P. Crocquet-Valdes, and D. H. Walker. 1997. Cloning and sequencing of the gene for a 120-kDa immunodominant protein of *Ehrlichia chaffeensis*. Gene 184:149–154.
25. Yu, X. J., P. A. Crocquet-Valdes, L. C. Cullman, V. L. Popov, and D. H. Walker. 1999. Comparison of *Ehrlichia chaffeensis* recombinant proteins for serologic diagnosis of human monocytotropic ehrlichiosis. J. Clin. Microbiol. 37:2568–2575.
26. Yu, X. J., J. W. McBride, C. M. Diaz, and D. H. Walker. 2000. Molecular cloning and characterization of the 120-kilodalton protein gene of *Ehrlichia canis* and application of the recombinant 120-kilodalton protein for serodiagnosis of canine ehrlichiosis. J. Clin. Microbiol. 38:369–374.
27. Yu, X. J., J. W. McBride, and D. H. Walker. 1999. Genetic diversity of the 28-kilodalton outer membrane protein gene in human isolates of *Ehrlichia chaffeensis*. J. Clin. Microbiol. 37:1137–1143.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. DNA encoding *Ehrlichia canis* immunoreactive surface protein P43, said protein having an amino acid sequence of SEQ ID No: 2, wherein said DNA is selected from the group consisting of:

(a) isolated DNA which encodes said P43 protein;

(b) isolated DNA which hybridizes to isolated DNA of (a) above under high stringency conditions consisting of hybridization at 42° C. in the presence of about 50% formamide, a first wash at 65° C. with 2×SSC containing 1% SDS and a second wash at 65° C. with 0.1× SSC, and which encodes said P43 protein; and (c) isolated DNA differing from the isolated DNAs of (a) and (b) above in codon sequence due to the degeneracy of the genetic code, and which encodes said P43 protein having an amino acid sequence of SEQ ID No: 2.

2. The DNA of claim 1, wherein said DNA has the sequence shown in SEQ ID No:1.

3. A vector comprising the DNA of claim 1 and regulatory elements necessary for expression of the DNA in a cell.

4. A host cell transfected with the vector of claim 3, said vector expressing said P43 protein.

5. The host cell of claim 4, wherein said cell is selected from group consisting of bacterial cells, mammalian cells, plant cells and insect cells.

6. The host cell of claim 5, wherein said bacterial cell is *E. coli*.

* * * * *

UNITED STATES PATENT AND TRADEMARK OFFICE
CERTIFICATE OF CORRECTION

PATENT NO. : 6,355,777 B1
DATED : March 12, 2002
INVENTOR(S) : David H. Walker and Jere W. McBride It is certified that error appears in the above-identified patent and that said Letters Patent is hereby corrected as shown below:

Column 4,
Line 3, please delete the comma after the word "Freshney".

Column 5,
Line 5, please insert a period after "J".

Column 8,
Line 3, please insert a period after "No. 2".
Line 16, please insert a space between "SEQ ID NO:" and "2".

Column 11,
Line 3, please insert a period after "min".
Line 8, "hr" should read -- hour --.
Line 40, please insert a period after "min".
Line 44, please insert a period after "min".
Line 62, please insert a space after "magnifications".
Line 66, please hyphenate "Forty two".

Column 12,
Line 36, in Table 1, please delete "bleed-".

Column 14,
Line 20, "h" should read -- hour --.

Column 17,
Line 30, "i n" should read -- in --.

UNITED STATES PATENT AND TRADEMARK OFFICE
CERTIFICATE OF CORRECTION

PATENT NO. : 6,355,777 B1
DATED : March 12, 2002
INVENTOR(S) : David H. Walker and Jere W. McBride It is certified that error appears in the above-identified patent and that said Letters Patent is hereby corrected as shown below:

Column 19,
Line 8, please insert a space before the words "a potential".

Signed and Sealed this

Twenty-third Day of July, 2002

Attest:

Attesting Officer

JAMES E. ROGAN
Director of the United States Patent and Trademark Office

SEQUENCE LISTING

```
<160> NUMBER OF SEQ ID NOS: 12

<210> SEQ ID NO 1
<211> LENGTH: 1173
<212> TYPE: DNA
<213> ORGANISM: Ehrlichia Canis
<220> FEATURE:
<221> NAME/KEY: CDS
<222> LOCATION: 1..1173
<223> OTHER INFORMATION: P43 Antigen of Ehrlichia Canis

<400> SEQUENCE: 1
```

-continued

```
atgtcagatc caaacaagg tgatccagaa caaaatcaaa ctaaccctag tggtgatatt        60
caggatcaaa gtcagcaaga tcaacaggaa caagatcagc agcagggagc agttggtggt      120
gctgttggta atagtcctat tgaaagagag agagtagctg ctcctgagag tgaagattta      180
tatactgtga ttatacctaa gggtaaaaga actgctgctc caattttgga agaaagtct       240 cctactcctg aaccgaaagt agaagatgat gaagatttac ctcctacatt accgccaaga      300
acattttcag gagaaggata tgatgacgtt ggagttagta tgcctactgt tagtcgtggc      360 ataccaac ctcccatagt tcaagatagt aatctatatt caagtattgg tggcgtacca       420
caagaagcac aatatgatgc agcagctcgg gctggtgggc aagaaagtt tttgtatggg      480 ccatatacat tcagtaatgg tcaggaaatt atggactttg aatttgatac tccttggcca      540
gatgttagga atgcagtttt aggtaataaa gagataaaag aagagtggtt aactacttct      600
gggccagtac gtgatattgc tgataggata gttgcttcta aggtgattt gtctgaggat       660 caagtagaag aaatccttga tattatattt atgaatgaat cagaaatcgc tgaaggtatt      720
tctaatccat tacatgctga tgttgataat aatcctgtta aggtgctaa gaatgtgatg       780 acattgatgc atctagttta tgcatgtgat gttgatccac gtatagtaaa agctttagga      840
gaggtggaaa atgatgaagg tgatttagga gctaatgctt ataatgtttt agatagtgag      900
ggtaatcttc ctttacatca tgctgcaaag aattgtacag gggataagtt aaagctttgt      960
atggagaaaa caaagactga ttttattgat actgcaaatt ttgcgaatca atccccttta     1020
catattatta cacagaagcc agattgttct gtattagata ttgaagagtt tacaagccgt     1080
aatttagatt ttggacttgt agatggagat ggtaaaaatc ctttacatca tgctgttgaa     1140
catttgccac ctgttaactt aaagggggcgg taa                                 1173
```

<210> SEQ ID NO 2
<211> LENGTH: 390
<212> TYPE: PRT
<213> ORGANISM: Ehrlichia Canis
<220> FEATURE:
<223> OTHER INFORMATION: P43 Antigen of Ehrlichia Canis

<400> SEQUENCE: 2

```
Met Ser Asp Pro Lys Gln Gly Asp Pro Glu Gln Asn Gln Thr Asn
                 5                  10                  15

Pro Ser Gly Asp Ile Gln Asp Gln Ser Gln Gln Asp Gln Gln Glu
                20                  25                  30

Gln Asp Gln Gln Gln Gly Ala Val Gly Gly Ala Val Gly Asn Ser
                35                  40                  45

Pro Ile Glu Arg Glu Arg Val Ala Ala Pro Glu Ser Glu Asp Leu
                50                  55                  60

Tyr Thr Val Ile Ile Pro Lys Gly Lys Arg Thr Ala Ala Pro Ile
                65                  70                  75

Leu Glu Arg Lys Ser Pro Thr Pro Glu Pro Lys Val Glu Asp Asp
                80                  85                  90

Glu Asp Leu Pro Pro Thr Leu Pro Pro Arg Thr Phe Ser Gly Glu
                95                 100                 105

Gly Tyr Asp Asp Val Gly Val Ser Met Pro Thr Val Ser Arg Gly
               110                 115                 120

Ile Tyr Gln Pro Pro Ile Val Gln Asp Ser Asn Leu Tyr Ser Ser
               125                 130                 135

Ile Gly Gly Val Pro Gln Glu Ala Gln Tyr Asp Ala Ala Ala Arg
```

```
                    140                 145                 150
Ala Gly Gly Pro Arg Lys Phe Leu Tyr Gly Pro Tyr Thr Phe Ser
                155                 160                 165
Asn Gly Gln Glu Ile Met Asp Phe Glu Phe Asp Thr Pro Trp Pro
            170                 175                 180
Asp Val Arg Asn Ala Val Leu Gly Asn Lys Glu Ile Lys Glu
        185                 190                 195
Trp Leu Thr Thr Ser Gly Pro Val Arg Asp Ile Ala Asp Arg Ile
            200                 205                 210
Val Ala Ser Lys Gly Asp Leu Ser Glu Asp Gln Val Glu Glu Ile
            215                 220                 225
Leu Asp Ile Ile Phe Met Asn Glu Ser Glu Ile Ala Glu Gly Ile
            230                 235                 240
Ser Asn Pro Leu His Ala Asp Val Asp Asn Asn Pro Val Lys Gly
            245                 250                 255
Ala Lys Asn Val Met Thr Leu Met His Leu Val Tyr Ala Cys Asp
            260                 265                 270
Val Asp Pro Arg Ile Val Lys Ala Leu Gly Glu Val Glu Asn Asp
            275                 280                 285
Glu Gly Asp Leu Gly Ala Asn Ala Tyr Asn Val Leu Asp Ser Glu
            290                 295                 300
Gly Asn Leu Pro Leu His His Ala Ala Lys Asn Cys Thr Gly Asp
            305                 310                 315
Lys Leu Lys Leu Cys Met Glu Lys Thr Lys Thr Asp Phe Ile Asp
            320                 325                 330
Thr Ala Asn Phe Ala Asn Gln Ser Pro Leu His Ile Ile Thr Gln
            335                 340                 345
Lys Pro Asp Cys Ser Val Leu Asp Ile Glu Glu Phe Thr Ser Arg
            350                 355                 360
Asn Leu Asp Phe Gly Leu Val Asp Gly Asp Gly Lys Asn Pro Leu
            365                 370                 375
His His Ala Val Glu His Leu Pro Pro Val Asn Leu Lys Gly Arg
            380                 385                 390
```

<210> SEQ ID NO 3
<211> LENGTH: 16
<212> TYPE: DNA
<213> ORGANISM: Artificial Sequence
<220> FEATURE:
<223> OTHER INFORMATION: Hpa I & HinP1/EcoRI conversion adapter 1,
    A1 (upper strand)

<400> SEQUENCE: 3
gcttccccaa gcttaa                                                    16

<210> SEQ ID NO 4
<211> LENGTH: 14
<212> TYPE: DNA
<213> ORGANISM: Artificial Sequence
<220> FEATURE:
<223> OTHER INFORMATION: Hpa I & HinP1/EcoRI conversion adapter 1,
    B1 (lower strand)

<400> SEQUENCE: 4
gcttggggaa gcgc                                                      14

<210> SEQ ID NO 5
<211> LENGTH: 17

```
<212> TYPE: DNA
<213> ORGANISM: Artificial Sequence
<220> FEATURE:
<223> OTHER INFORMATION: Hpa I & HinP1/EcoRI conversion adapter 2,
      A2 (upper strand)

<400> SEQUENCE: 5
gcttccccaa gccttaa                                                    17

<210> SEQ ID NO 6
<211> LENGTH: 15
<212> TYPE: DNA
<213> ORGANISM: Artificial Sequence
<220> FEATURE:
<223> OTHER INFORMATION: Hpa I & HinP1/EcoRI conversion adapter 2,
      B2 (lower strand)

<400> SEQUENCE: 6
ggcttgggga agcgc                                                      15

<210> SEQ ID NO 7
<211> LENGTH: 18
<212> TYPE: DNA
<213> ORGANISM: Artificial Sequence
<220> FEATURE:
<223> OTHER INFORMATION: Hpa I & HinP1/EcoRI conversion adapter 3,
      A3 (upper strand)

<400> SEQUENCE: 7
gcttccccaa gcccttaa                                                   18

<210> SEQ ID NO 8
<211> LENGTH: 16
<212> TYPE: DNA
<213> ORGANISM: Artificial Sequence
<220> FEATURE:
<223> OTHER INFORMATION: Hpa I & HinP1/EcoRI conversion adapter 3,
      B3 (lower strand)

<400> SEQUENCE: 8
gggcttgggg aagcgc                                                     16

<210> SEQ ID NO 9
<211> LENGTH: 22
<212> TYPE: DNA
<213> ORGANISM: Artificial Sequence
<220> FEATURE:
<223> OTHER INFORMATION: Forward primer ECa43BADf

<400> SEQUENCE: 9
atgtcagatc caaaacaagg tg                                              22

<210> SEQ ID NO 10
<211> LENGTH: 24
<212> TYPE: DNA
<213> ORGANISM: Artificial Sequence
<220> FEATURE:
<223> OTHER INFORMATION: Reverse primer ECa43BADr

<400> SEQUENCE: 10
tccatctaca agtccaaaat ctaa                                            24

<210> SEQ ID NO 11
<211> LENGTH: 26
<212> TYPE: DNA
<213> ORGANISM: Artificial Sequence
<220> FEATURE:
```

```
<223> OTHER INFORMATION: Forward PCR primer p43-274f

<400> SEQUENCE: 11
gaaccgaaag tagaagatga tgaaga                                            26

<210> SEQ ID NO 12
<211> LENGTH: 21
<212> TYPE: DNA
<213> ORGANISM: Artificial Sequence
<220> FEATURE:
<223> OTHER INFORMATION: Reverse PCR primer p43-1185r

<400> SEQUENCE: 12
taagttaaca ggtggcaaat g                                                 21
```